US008588928B2

(12) United States Patent
Lehmann et al.

(10) Patent No.: US 8,588,928 B2
(45) Date of Patent: Nov. 19, 2013

(54) ACTIVE ELECTRODE STATE CONTROL SYSTEM WITH CURRENT COMPENSATION TO REDUCE RESIDUAL DC/LF VOLTAGE

(75) Inventors: Torsten Lehmann, Earlwood (AU); Paul Carter, Wesr Pennant Hills (AU); Christopher van den Honert, Aurora, CO (US); Ibrahim Ibrahim, North Ryde (AU); Tony M. Nygard, Terrigal (AU)

(73) Assignee: Cochlear Limited, Macquarie University, NSW (AU)

( * ) Notice: Subject to any disclaimer, the term of this patent is extended or adjusted under 35 U.S.C. 154(b) by 405 days.

(21) Appl. No.: 12/682,780

(22) PCT Filed: Oct. 10, 2008
(Under 37 CFR 1.47)

(86) PCT No.: PCT/AU2008/001506
§ 371 (c)(1),
(2), (4) Date: Sep. 15, 2010

(87) PCT Pub. No.: WO2009/046502
PCT Pub. Date: Apr. 16, 2009

(65) Prior Publication Data
US 2011/0178579 A1 Jul. 21, 2011

(30) Foreign Application Priority Data
Oct. 12, 2007 (AU) .............................. 2007905586

(51) Int. Cl.
*A61N 1/36* (2006.01)
(52) U.S. Cl.
USPC .................. 607/62; 607/13; 607/57

(58) Field of Classification Search
USPC ............................................. 607/13
See application file for complete search history.

(56) References Cited

U.S. PATENT DOCUMENTS

| 4,141,359 A | * | 2/1979 | Jacobsen et al. ................ 604/20 |
| 4,343,312 A | * | 8/1982 | Cals et al. ....................... 607/13 |
| 4,532,930 A | | 8/1985 | Crosby et al. |
| 4,811,738 A | * | 3/1989 | Economides et al. .......... 607/13 |
| 5,324,316 A | | 6/1994 | Schulman et al. |
| 5,603,725 A | | 2/1997 | Schaldach |

(Continued)

FOREIGN PATENT DOCUMENTS

| DE | 102004059973 A1 | 6/2006 |
| EP | 0241101 A1 | 10/1987 |
| EP | 1384434 A1 | 1/2004 |
| WO | 9721324 A1 | 6/1997 |

OTHER PUBLICATIONS

International Search Report for PCT/AU2008/001506, dated Nov. 25, 2008.
Written Opinion. PCT/AU2008/001506. Mailed Nov. 11, 2008.

*Primary Examiner* — Kennedy Schaetzle
(74) *Attorney, Agent, or Firm* — Kilpatrick, Townsend & Stockton, LLP.

(57) ABSTRACT

A body stimulating device operatively adapted to provide electrical stimuli within a body, the device including stimulating electrodes, stimulus generator, and electrode voltage sensors, said electrode voltage sensors operatively measuring the DC/LF voltage of the electrodes, wherein if the sensors determine that the electrode voltage for an electrode is outside a predetermined range, then a compensating current is applied to that electrode, so as to reduce the voltage.

16 Claims, 8 Drawing Sheets

(56) References Cited

U.S. PATENT DOCUMENTS

| | | | |
|---|---|---|---|
| 5,674,264 A * | 10/1997 | Carter et al. | 607/57 |
| 6,219,580 B1 | 4/2001 | Faltys et al. | |
| 6,600,955 B1 | 7/2003 | Zierhofer | |
| 6,895,278 B1 | 5/2005 | Gordon | |
| 7,277,751 B2 * | 10/2007 | Dupelle et al. | 607/4 |
| 2004/0267344 A1 * | 12/2004 | Stett et al. | 607/141 |
| 2006/0224199 A1 * | 10/2006 | Zeijlemaker | 607/11 |
| 2008/0015641 A1 | 1/2008 | Armstrong et al. | |

* cited by examiner

ACTIVE ELECTRODE STATE CONTROL SYSTEM WITH CURRENT COMPENSATION TO REDUCE RESIDUAL DC/LF VOLTAGE

CROSS-REFERENCE TO RELATED APPLICATIONS

This application is a National Stage Application under 35 USC §371(c) of PCT Application No. PCT/AU2008/001506, entitled "ACTIVE ELECTRODE STATE CONTROL SYSTEM," filed Oct. 10, 2008, which claims priority to Australian Provisional Application No. 2007905586, filed Oct. 12, 2007 all of which are hereby incorporated by reference herein.

BACKGROUND

1. Field of the Invention

The present invention relates to systems, methods and devices for controlling the states of stimulating electrodes in body stimulating devices, such as cochlear implants and other neural stimulators.

2. Related Art

Figure 1:
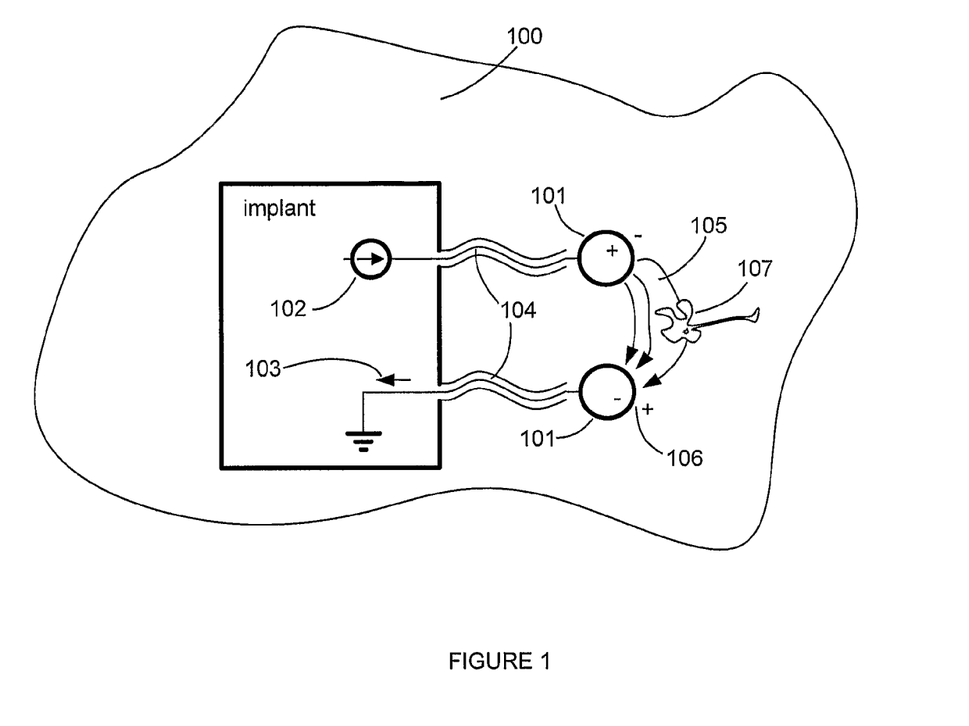
FIG. 1 is a conceptual drawing illustrating the passage of current using stimulating electrodes.

Electronic devices implanted within the body in order to stimulate nerve tissue (e.g. cochlear implants) for perceptual or functional purposes generally use platinum electrodes as the interface between the electronics and the body tissue. In general terms, such electrodes are selectively driven with a current in order to evoke a perception (for example sound) or a function (for example a limb movement) in the user. FIG. 1 illustrates this schematically. The platinum electrodes 101 are connected to the implant via insulated wires 104 and driven by the stimulating current 102, which passes through the tissue 100 and the nerve cell 107, and returns to the implant (return current 103). At the surface of the platinum electrodes 101, chemical reactions take place, changing the electron current in the electronics to an ion current 105 in the tissue; charge 106 remains on the electrode surface, causing an increase in voltage across the interface.

Under normal operation of the interface, these chemical reactions are reversible and when the current direction is changed, the reactions are reversed, leaving a neutral interface. It is usual for the stimuli to be structured as biphasic pulses, in such a way that there is no net charge delivered to the tissue. If, however, the current is allowed to flow in one direction for too long, toxic products can escape the interface and damage or destroy the surrounding tissue. Likewise, if the voltage across the interface is allowed to remain elevated for too long, toxic species are irreversibly generated at the interface. To ensure, then, that stimulation is safe, and that no toxic species escape the interface, it must be ensured that the DC and low-frequency (LF) states of the electrodes, i.e. the DC/LF interface voltages and the DC/LF interface currents, remain within certain bounds. The usual target values are some hundreds of milli-volts, or some tens of nano-amperes (for typical cochlear implant electrode areas of about 0.25 $mm^2$).

The FDA in the US requires that the magnitude of the current through an electrode is below 100 nA measured over any 1 ms period. The use of charge-neutral pulses ensures, in principle, that the FDA requirement for the DC/LF current is met; in practice, however there will be a small error in the generated stimulation current. This requires a second measure to be taken to ensure low levels of DC/LF current at all times. This is particularly an issue when high stimulation rates and high current levels are used. Further, if the stimulation current source goes out of compliance, then significant charge errors can occur.

A number of approaches are currently employed to control the interface voltage and current.

Figure 2:
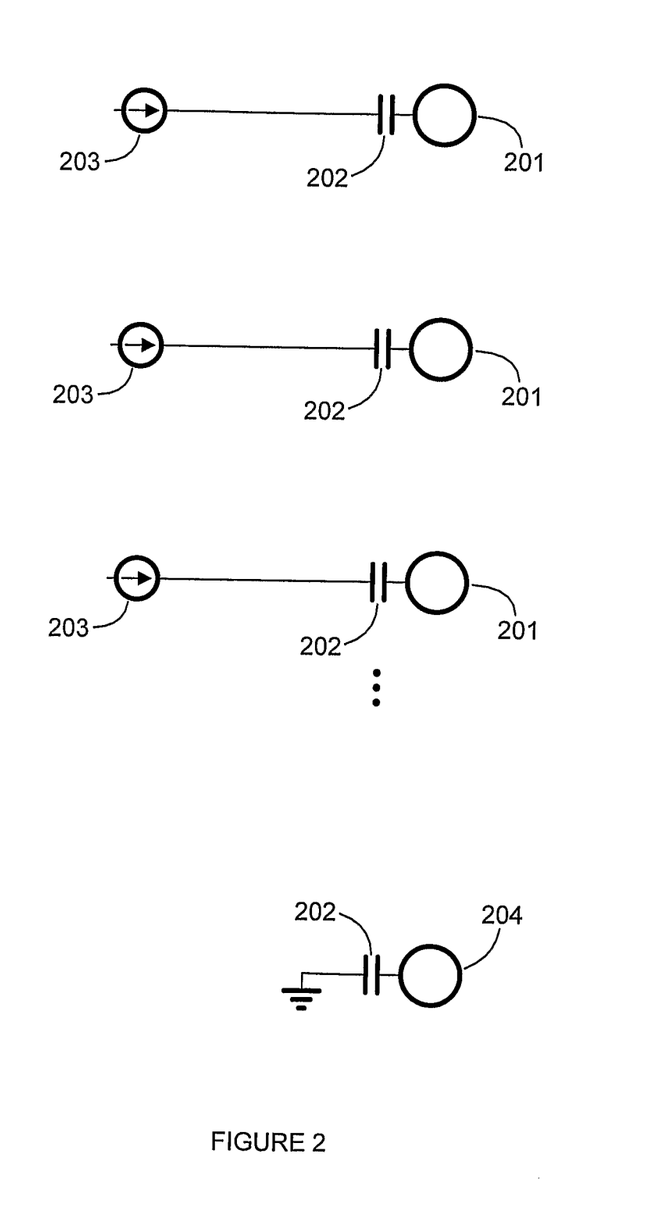
FIG. 2 illustrates a prior art DC blocking capacitor approach.

One approach is to use DC blocking capacitors for each electrode to ensure zero DC currents through the electrodes. FIG. 2 shows such an arrangement, whereby for each stimulating electrode 201, there is a DC blocking capacitor 202 disposed in the path for stimulation currents 203. A capacitor may also be disposed on the monopolar return electrode 204. In order for this approach to be effective, it is necessary to provide a capacitor with relatively high capacitance, in the nano-farad range, for each electrode. With current capacitor technology, this cannot be fabricated in an integrated circuit, and so discrete components are required to be used. It is difficult to have a capacitor per electrode when tens of electrodes are in use, as this requires tens of capacitors, which significantly increases the required space for the implant. As the number of electrodes increase in future devices, potentially to hundreds or thousands, DC blocking capacitors become even more impractical. This type of approach is known from, for example, U.S. Pat. No. 5,324,316 to Schulman et al., U.S. Pat. No. 6,600,955 to Zierhofer et al., and U.S. Pat. No. 6,219,580 to Faltys et al.

Figure 3:
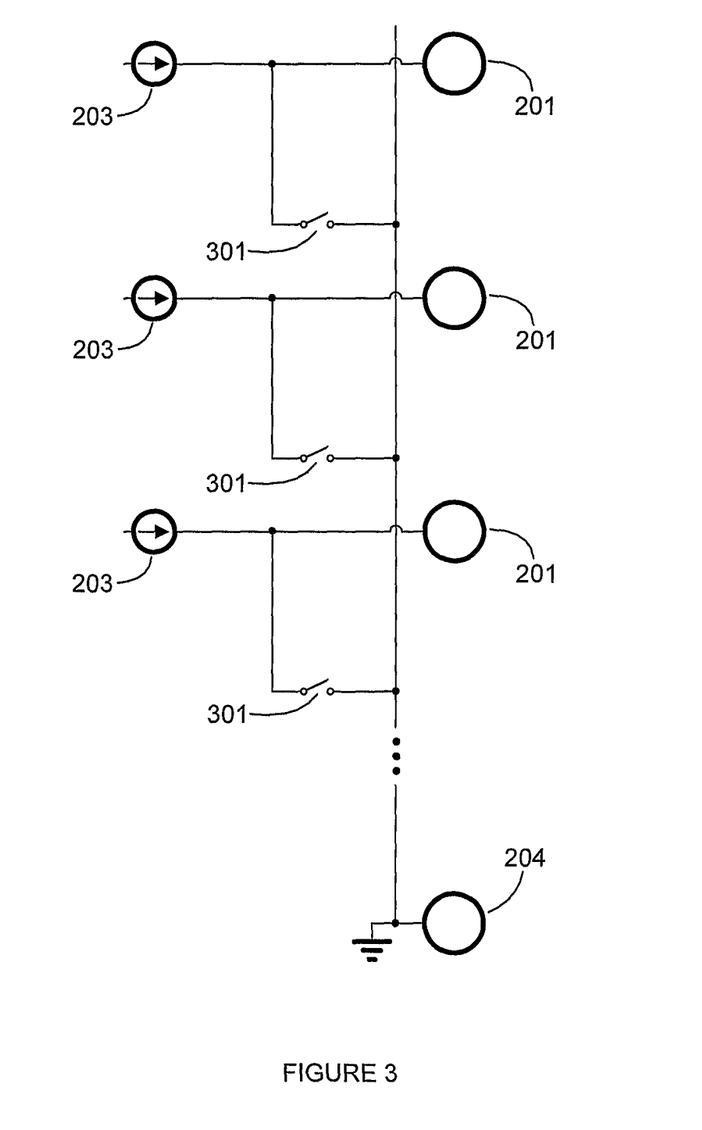
FIG. 3 illustrates a prior art shorting approach.

Another approach is to use periodic short-circuiting of all electrodes to ensure that the DC/LF electrode voltage does not drift out of the safe window. FIG. 3 illustrates schematically such an arrangement, whereby a shorting switch 301 is provided for each electrode 201, and periodically the switches are closed. In some implementations, a series capacitor is used in the return electrode only. This approach allows for up-scaling of the number of electrodes. However, shorting all the electrodes requires the stimulation protocol to include an inactive period when no stimulation takes place. This approach is disclosed in European Patent No. 0,241,101 to Cochlear Limited.

Another approach is to measure the differential residual voltage between electrodes during a dead period and adjust the duration or amplitude of the applied stimuli to compensate for the charge error. This approach is disclosed in U.S. Pat. No. 5,674,264 to Cochlear Limited.

Using high-frequency asynchronous stimulation on many electrodes concurrently, and employing electrode arrays with a large number of electrodes, are considered by many as desirable in order to improve system performance in cochlear implants, and other implant systems. When concurrent, asynchronous stimulation is used, there is no dead period available to carry out electrode shorting.

SUMMARY

In one aspect of the present invention, there is provided a method of controlling DC/LF voltage in a body stimulating electrode system, the method comprising: measuring the residual DC/LF voltage associated with each stimulating electrode; and if a residual voltage is outside a predetermined range, then applying a compensating current of opposite polarity to reduce the residual voltage.

In another aspect, there is provided a body stimulating device, operatively adapted to provide electrical stimuli with in a body, the device including stimulating electrodes, a stimulus generator, and electrode voltage sensors, said electrode voltage sensors operatively measuring the DC/LF voltage of the electrodes, wherein if the sensors determine that the electrode voltage for an electrode is outside a predetermined range, then a compensating current is applied to that electrode, so as to reduce the voltage.

BRIEF DESCRIPTION OF THE DRAWINGS

Embodiments of the present invention are described below with reference to the attached drawings, in which.

DETAILED DESCRIPTION

Embodiments will be disclosed that provide a system in which the state of the stimulating electrodes is monitored in an ongoing way, and the states are actively corrected if they fall outside a predetermined window. As will be discussed below, these embodiments may allow for stimulation without a periodic 'dead' period, to facilitate for example asynchronous stimulation on multiple electrodes. This approach also removes the requirement for a capacitor for each electrode.

It will be appreciated that while embodiments of the present invention will be described principally in the context of a particular implementation for a cochlear implant, it is applicable wherever electrical stimulation is to be delivered within the body, either from an implanted device, or from an externally disposed device. Whilst it is most clearly applicable to neural stimulation, the present invention can be applied to any other form of electrical stimulation applied to the body.

Figure 5:
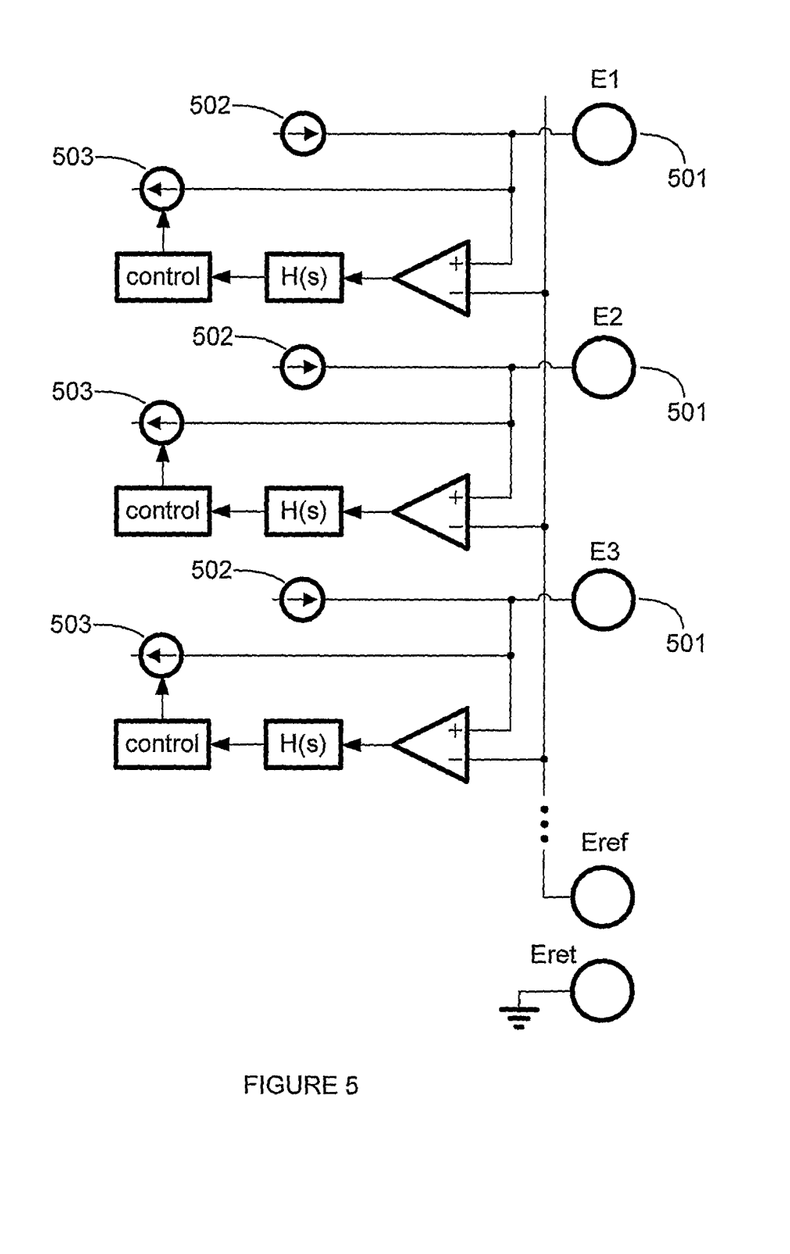
FIG. 5 is a schematic illustration of one embodiment of the present invention.
Figure 5A:
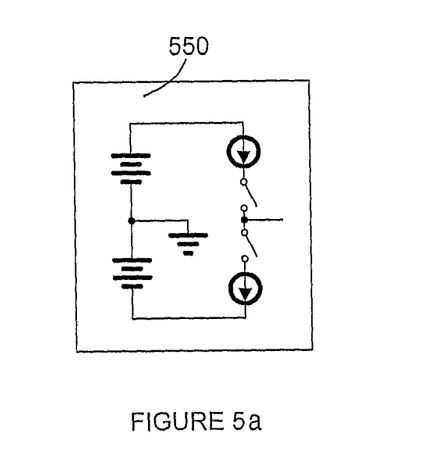
FIG. 5a is a schematic illustration of one embodiment of a stimulation current source of FIG. 5.

FIG. 5 illustrates one embodiment of the present invention. Electrodes 501 are generally designated as E. A stimulation current from a stimulation current source 550, shown in FIG. 5a, is (selectively) applied to each stimulating electrode 501. At each electrode, the electrode voltage is compared to a reference electrode Eref which does not carry any current, using a suitable differential amplifier. The same reference electrode Eref may be used for all the stimulating electrodes. The amplifier output passes through a filter H(s) (the operation of which will be described below) and then into a control circuit. Similarly to the electrode shorting approach, the electrode DC/LF voltage for each electrode is controlled—however, instead of using a passive shorting action during an inactive time-slot, an active feed-back system using stimulating currents 502 and compensation currents 503 controls the electrode voltage. No specific time slot is required for the voltage control step.

Figure 5B:
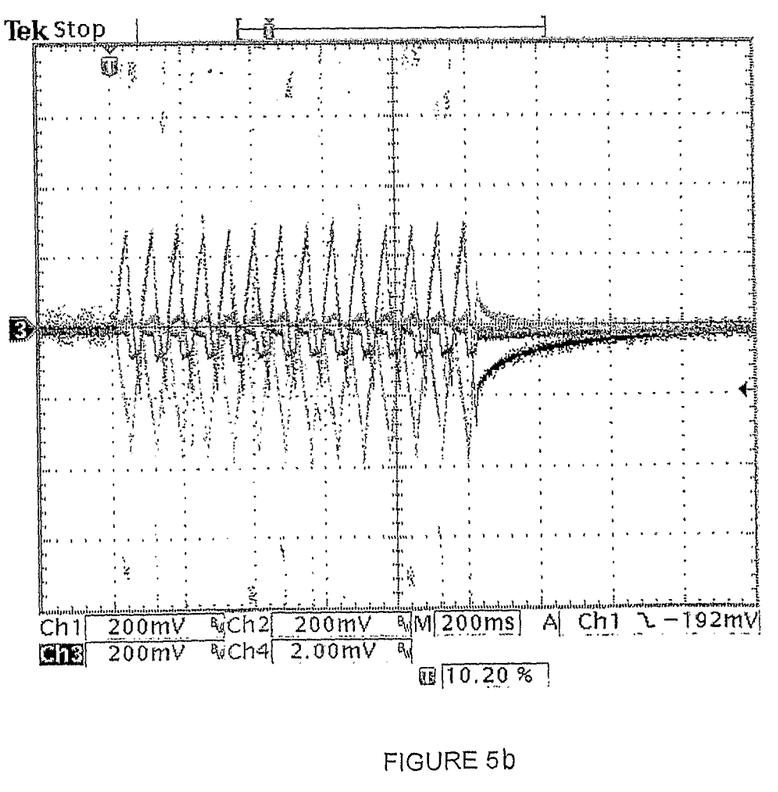
FIG. 5b is a graph showing the experimental result of an embodiment in accordance with FIG. 5.

FIG. 5b shows an experimental result of the embodiment according to FIG. 5 with the following parameters:

Linear 12 dB/octave roll-off low-pass filters with corner frequency of 15 Hz.

Compensation currents in fixed times of 1 ms delivered (asynchronously with the stimulation currents) in the appropriate direction when the low-pass filtered electrode voltages drift outside the set compensation voltage thresholds.

Experiments were carried out using a Cochlear electrode array submerged in physiological saline. FIG. 5b shows traces of the electrode voltages over a 200 ms period when:

One pair of electrodes is driven with 1 mA unblalanced biphasic pulses of 10 μs/phase and a 1 ms repetition rate, having an equivalent net DC current of 10 μA; the stimulation is carried out for 100 ms.

The compensation current magnitude is set to 20 μA, while the compensation voltage threshold is set to 100 mV.

As shown, the compensation feed-back loop keeps the low-frequency voltages on all electrodes within a window about 400 mV.

Figure 6:
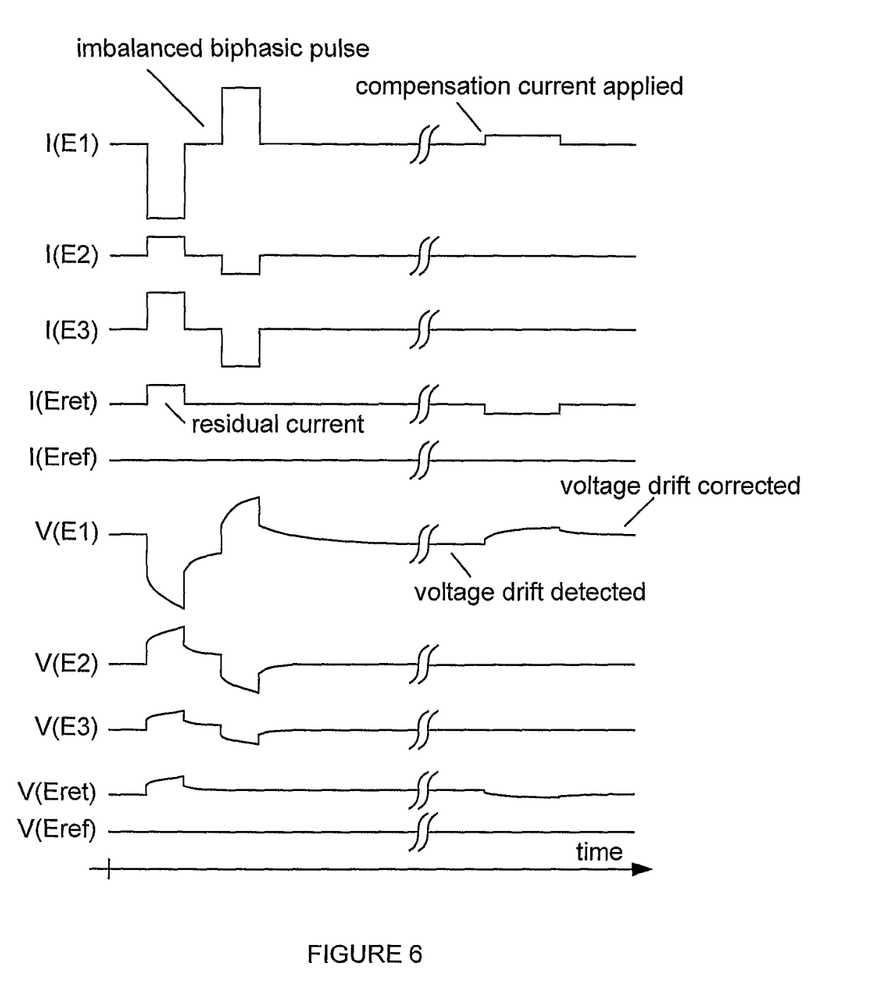
FIG. 6 illustrates timing of currents and voltages during operation of one embodiment of the present invention.

FIG. 6 is a timing diagram illustrating the process whereby three stimulating electrodes (E1, E2 and E3) are simultaneously being driven with typical bi-phasic current pulses, but the pulse on E1 has a DC component (nonzero net charge); this causes the voltage on the electrode V (E1) to build up. This build up is detected by the control system and a compensation pulse on E1 is applied to bring back the voltage. During stimulation large (up to tens of volts) voltages appear on the electrodes; such voltages are a necessary part of the stimulation and must be removed before the electrode voltage is passed to the feedback control system. To this end, an appropriate filter (H(s)) is used as seen in FIG. 5. The implementation shown in FIG. 5 uses local controls for each electrode.

The filter transfer function, H(s), needs to be chosen such that stimulation artifacts are suppressed while voltage drift is detected before it can cause harm. The simplest approach is to use a linear, time-invariant low-pass filter. While the stimulation current pulse is typically in the 10 μs-100 μs range for cochlear implants, the duration of the electrode voltage response to the stimulation current is in the 1 ms range. Non-zero voltages should not persist on the interface for more than about 100 ms; as such, the filter cut-off frequency, fcc should lie between 1 kHz and 10 Hz. A second or higher order (NLP) filter is therefore preferred with a (programmable) cut-off frequency of about 100 Hz.

It will be understood that these values are appropriate for a cochlear implant of standard design—other devices or differing designs may require different values as will be apparent to those skilled in the art. It will also be understood that there are many different implementations and designs for filters which can be selected as appropriate for the device in question.

When performing simultaneous stimulation on many electrodes, it is in practice, due to mismatch in the current sources, impossible to ensure an exact net zero current being delivered to the tissue. The use of a common return electrode provides a current path for the residual current (see FIG. 5). The return electrode can also be used as a return current path for deliberate non-zero net stimulation currents (i.e., monopolar stimulations in the case of only one stimulating electrode) to enhance current flow across the nerves. For cochlear implants, the preferred form of the return electrode is a relatively large extracochlear electrode (typically in the range of 1 mm$^2$ to 10 mm$^2$). Another function of the return electrode is to define the DC potential between the implant and the tissue (the implant ground); without such a measurement, this value would be undefined, as all other connections between the implant and tissue are high impedance. Such connections create compliance issues on sinking or sourcing stimulation currents (see FIG. 4 and previous discussion in relation to FIGS. 5 and 6). Note that even though significant currents may pass through the return electrode, it does not need a compensation current circuit: if all other stimulating electrodes are monitored, having near to net zero DC currents, the DC current in the return electrode must, by virtue of Kirchhoff's current law, also be near zero. Observing the DC voltage on the return electrode, however will provide information about failures in the active compensation, and for this reason, the voltage should be measured as it is on the stimulating electrodes according to the present embodiment.

In order to measure the voltage across an electrode, to determine whether a compensation current needs to be applied to that electrode, the tissue potential must be known. To this end, it is required to use a reference electrode which is in contact with the tissue, but never has any current flowing in it; this electrode will give a reliable measurement of the tissue potential. All the electrodes should be formed from the same material such that the half-cell potential across each electrode is the same. This electrode should preferably be large in surface area (similar to the extra-cochlear return electrode), such that its impedance is relatively small.

A convenient location for a large reference electrode in cochlear implants is outside the cochlea; i.e. an exiting extra-cochlear electrode which does not participate in the stimulations could be used or, alternatively, a dedicated electrode could be added to the system. Another suitable choice for the reference electrode is a parallel combination of unused electrodes in the intracochlear electrode array. If the reference electrode is place outside the cochlea, this may create an offset in the safe stimulation electrode DC voltage window (see below), due to typical natural DC voltage differences between the intra-cochlear electrodes and extra-cochlear electrodes of some tens of milli-volts.

The magnitude of the compensation currents should be chosen such that they can compensate for the largest expected error in the stimulation current. For example: if the maximum stimulation current is $I_M=2$ mA, the stimulation phase length is $T_p=50$ µs, the minimum stimulation period on a particular electrode is $T_{SP}=500$ µs, and the maximum stimulation current error is $E=2\%$ (typical numbers for cochlear implants), the worst-case DC current induced by the stimulation is $$I_{DC}=I_M*T_P*E/T_{SP}=4 \text{ µA}$$

Note that this magnitude is well below normal stimulation thresholds in cochlear implants. It is highly desirable that the compensation currents be kept below the level of user perception.

Figure 7:
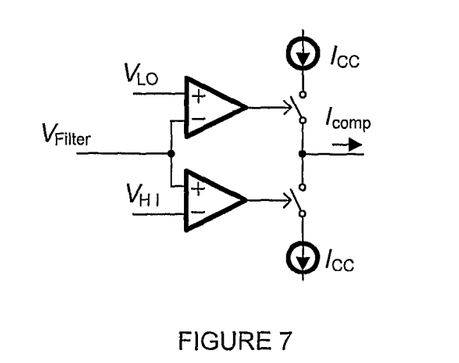
FIG. 7 illustrates an embodiment of a compensation current controller.

A simple way to control the delivery of the compensation current, $L_{comp}$ is by means of the circuit shown in FIG. 7. The output from the filter, $W_{Filter}$ is compared with a safe window (say $V_{LO}=-200$ mV and $V_{HI}=220$ mV) and whenever the voltage is outside this range, a constant current is delivered to the electrode to move the voltage back. The magnitude of this current, $I_{CC}$ should be chosen conservatively larger than the largest expected stimulation DC current; for the example above, maybe $I_{CC}=5$ µA.

Figure 4:
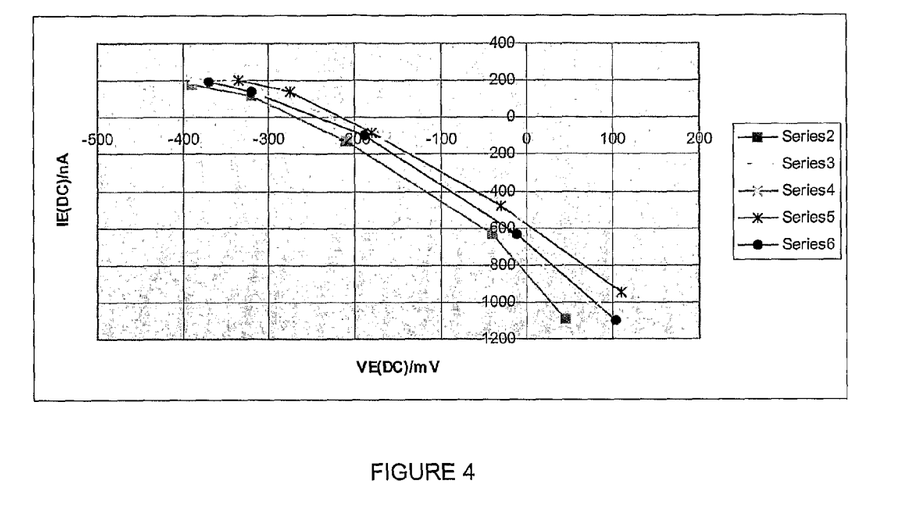
FIG. 4 is a graph showing a typical relationship between DC current and DC voltage for tissue under stimulation.

It is noted that, because of the non-linearities of the electrode-tissue interface, ensuring zero DC voltage and zero DC current cannot be achieved at the same time. FIG. 4 shows experimental data from a test where a pair of platinum electrodes was driven by a cochlear implant; the anodic phase length was varied, causing varying DC currents to be delivered during stimulation, while DC voltages and DC currents are being measured. The current in nano-amperes appears on the y axis, while voltage in milli-volts is shown on the x axis. It can be seen that zero voltage and zero current does not appear at the same time. At high stimulation rates (towards 2 kHz) and at high currents (towards 2 mA), the DC voltage corresponding to zero DC current increases in magnitude.

The electrode tissue interface has a complex, non-linear impedance; further, this impedance may vary significantly over time, from implantee to implantee, and from electrode to electrode. For this reason, it is difficult to a priori determine the optimum parameter set for the control system. In any practical system, it is critical that in-vivo data is acquired for system verification. Another consequence of these unknowns is that control loop may become unstable for particular electrode impedances. Thus, it is important that all key parameters are programmable. That is, it is recommended that Filter cut-off frequency ($F_{LP}$) should be programmable in the range 10 Hz-1 kHz.

Filter order (NLP) should be programmable as $1^{st}$, $2^{nd}$ and $3^{rd}$ order.

Compensation current magnitudes ($I_{CC}$) should be programmable in the range 100 nA-10 µA.

Compensation voltage thresholds ($V_{LO}$ and $V_{HI}$) should be programmable in the range −400 mV to 400 mV.

Figure 8:
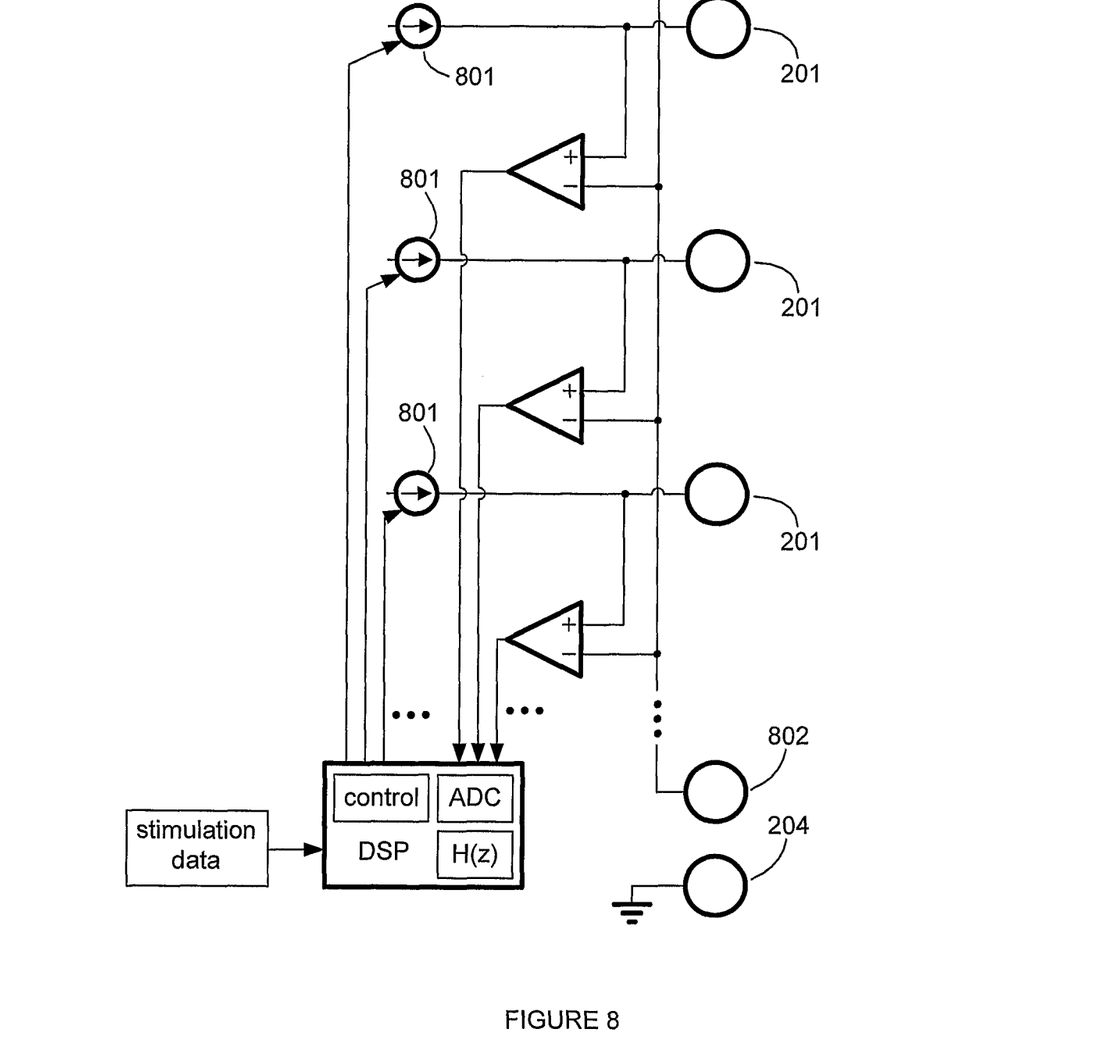
FIG. 8 is a schematic illustration of another embodiment of the present invention.

Most implantable neural stimulators now have significant digital signal processing capability. Thus, instead of using local hardware for each electrode to perform the compensation, data can be passed to a central DSP or microprocessor which acts on the data. This has the particular advantage that the compensation algorithm can be reprogrammed when more in-vivo data is available. FIG. 8 shows an example of this, with the most central architecture, where the raw, digitized (using a suitable analog-to-digital converter (ADC)) electrode voltage measurements are passed to the DSP, which performs filtering (H(z)) and implements the control algorithm. In as simplest form, the control algorithm would be the same as described above: each electrode filter output is compared with compensation voltage thresholds and, if the filter output lies outside the safe range, the need for and direction of a compensation current for that electrode is flagged. The compensation currents here are applied not via dedicated current sources but by perturbing the amplitude settings (received from the primary part of the system that calculates the stimulation data) on the stimulation current sources 801. In this embodiment the DC/LF voltage is extracted using filter H(z) and the charge error is determined in reference to the reference electrode 802 instead of synchronous sampling. Accordingly the amplitude of the asynchronous stimulation current may be adjusted without requiring a dead period. Other possible variations which could be implemented include:

Performing electrode voltage sensing and filtering at the electrode sites, passing the DC voltage to the DSP. This variation relaxes the requirements to the ADC.

Performing electrode voltage sensing, filtering and thresholding at the electrode sites, passing "out of range" information to the DSP. This variation eliminates the need for the ADC.

Using dedicated compensation current sources for each electrode controlled by the DSP. This variation relaxes the requirements to the stimulating current sources.

Using multiples (or a continuum) levels of compensation current depending on the electrode voltage error (using larger compensation current at higher voltage error). This variation enables a more advanced feed-back control system to be implemented.

Using non-linear filters before a subsequent linear filtering such that the large electrode voltages present during stimulation are largely ignored by the control system. This variation would seek to keep the median, rather than the average, electrode voltage within the given bounds.

While the present invention has been described with respect to specific embodiments, it will be appreciated that various modifications and changes could be made without departing from the scope of the invention.

The invention claimed is:

1. A method of controlling DC/LF voltage in a body stimulating electrode system, the method comprising:
   measuring the residual DC/LF voltage between each stimulating electrode and body tissue;
   if a residual voltage is outside a predetermined range, then applying a compensating current of opposite polarity to reduce the residual voltage.

2. The method according to claim 1, wherein the residual voltage is measured relative to a reference electrode operatively in electrical contact with body tissue, which does not carry a current.

3. The method according to claim 1, wherein the measured voltage is filtered so as to suppress stimulation artifacts.

4. The method according claim 1, wherein a feedback control system is provided and associated with each stimulating electrode.

5. The method according to claim 1, wherein a central control arrangement is provided to control the compensating currents.

6. The method according to claim 5, wherein the central control arrangement also controls the stimulating currents.

7. A method of controlling DC/LF voltage in a body stimulating electrode system, the method comprising:
   measuring the residual DC/LF voltage associated with each stimulating electrode;
   if a residual voltage is outside a predetermined range, then applying a compensating current of opposite polarity to reduce the residual voltage;
   wherein the residual voltage is measured relative to a reference electrode operatively in electrical contact with body tissue, which does not carry a current;
   wherein the reference electrode has a relatively large surface area as compared to a surface area of each stimulating electrode.

8. The method according to claim 7, wherein the surface area of the reference electrode is at least about four times greater than the surface area of each stimulating electrode.

9. A body stimulating device, operatively adapted to provide electrical stimuli with in a body, the device including:
   stimulating electrodes,
   a stimulus generator, and
   electrode voltage sensors,
   said electrode voltage sensors operatively measuring the DC/LF voltage the electrodes and body tissue,
   wherein if the sensors determine that the electrode voltage for an electrode is outside a predetermined range, then a compensating current is applied to that electrode, so as to reduce the voltage.

10. The device according to claim 9, wherein each voltage sensor operates between a respective stimulating electrode and a reference electrode, operatively in electrical contact with body tissue, which does not carry a current.

11. The device according to claim 9, wherein the electrode voltage measured by each sensor is filtered so as to suppress stimulation artifacts.

12. The device according to claim 9, wherein a feedback control system is provided associated with each stimulating electrode.

13. The device according to claim 9, wherein a central processor is provided to control the compensating currents.

14. The device according to claim 13, wherein the central processor also controls the stimulus generator.

15. A body stimulating device, operatively adapted to provide electrical stimuli with in a body, the device including:
   stimulating electrodes,
   a stimulus generator, and
   electrode voltage sensors,
   said electrode voltage sensors operatively measuring the DC/LF voltage the electrodes and body tissue,
   wherein if the sensors determine that the electrode voltage for an electrode is outside a predetermined ran e then a compensation current is applied to that electrode so as to reduce the voltage;
   wherein each voltage sensor operates between a respective stimulating electrode and a reference electrode, operatively in electrical contact with body tissue, which does not carry a current; and
   wherein the reference electrode has a relatively large surface area as compared to a surface area of each stimulating electrode.

16. The device according to claim 15, wherein the surface area of the reference electrode is at least about four times greater than the surface area of each stimulating electrode.

\* \* \* \* \*

UNITED STATES PATENT AND TRADEMARK OFFICE
CERTIFICATE OF CORRECTION

PATENT NO.        : 8,588,928 B2                              Page 1 of 1
APPLICATION NO.   : 12/682780
DATED             : November 19, 2013
INVENTOR(S)       : Torsten Lehmann et al.

It is certified that error appears in the above-identified patent and that said Letters Patent is hereby corrected as shown below:

--In the Claims, Claim 15, Col. 8, Lines 29-30, please correct:

from "predetermined ran e then a compensation current is applied to that electrode"

to "predetermined range, then a compensation current is applied to that electrode,".

Signed and Sealed this
First Day of April, 2014

Michelle K. Lee
*Deputy Director of the United States Patent and Trademark Office*